United States Patent
Anderson et al.

(10) Patent No.: US 6,403,116 B1
(45) Date of Patent: Jun. 11, 2002

(54) COENZYME Q10 FORMULATION

(75) Inventors: Mark L. Anderson, Carmel, NY (US); Abdullah Kelker, Clifton, NJ (US)

(73) Assignee: Triarco Inductries, Inc., Paterson, NJ (US)

( * ) Notice: Subject to any disclaimer, the term of this patent is extended or adjusted under 35 U.S.C. 154(b) by 0 days.

(21) Appl. No.: 09/706,524

(22) Filed: Nov. 3, 2000

(51) Int. Cl.$^7$ ................................. A61K 47/00
(52) U.S. Cl. ............ 424/439; 424/400; 424/450; 424/451
(58) Field of Search ............... 424/400, 401, 424/49, 450, 451, 439

(56) References Cited

U.S. PATENT DOCUMENTS

| | | | |
|---|---|---|---|
| 4,112,946 A | 9/1978 | Herschler | 128/253 |
| 4,296,130 A | 10/1981 | Herschler | 424/337 |
| 4,483,873 A | 11/1984 | Ohashi et al. | 424/331 |
| 4,514,421 A | 4/1985 | Herschler | 514/711 |
| 4,568,547 A | 2/1986 | Herschler | 514/772 |
| 4,572,915 A | 2/1986 | Crooks | 514/458 |
| 4,616,039 A | 10/1986 | Herschler | 514/711 |
| 4,914,135 A | 4/1990 | Herschler | 514/711 |
| 5,891,853 A | 4/1999 | Shealy et al. | 514/23 |
| 5,989,583 A | 11/1999 | Amselem | 424/439 |
| 6,045,826 A | 4/2000 | Borowy-Borowski et al. | 424/451 |
| 6,056,971 A | 5/2000 | Goldman | 424/439 |
| 6,183,758 B1 * | 2/2001 | Scott | 424/401 |

FOREIGN PATENT DOCUMENTS

| | | |
|---|---|---|
| WO | 95/05164 | 2/1995 |

* cited by examiner

*Primary Examiner*—Thurman K. Page
*Assistant Examiner*—Charesse L. Evans
(74) *Attorney, Agent, or Firm*—Fitzpatrick, Cella, Harper & Scinto

(57) ABSTRACT

The invention relates to compositions comprising coenzyme Q10, methyl sulfonyl methane, citric acid, at least one polysorbate materials, and at least one water-soluble polysaccharide, and methods of administering nutritionally significant and/or therapeutically effective amounts of coenzyme Q10 in an oral formulation.

24 Claims, No Drawings

COENZYME Q10 FORMULATION

BACKGROUND OF THE INVENTION

1. Field of the Invention

This invention relates to compositions and methods for providing aqueous formulations of aqueous insoluble dietary supplements. In particular, this invention relates to compositions and methods for providing an aqueous formulation of the dietary supplement coenzyme Q10.

2. Related Background Art

Formulations of aqueous-insoluble dietary supplements are known in the art. Nutritional supplements incorporating lipophilic or fat-soluble essential nutrients such as vitamins or fatty acids are widely used in human and animal health care.

One compound receiving particular attention lately as a nutritional supplement and therapeutic agent is coenzyme Q10 ("Co-Q10"), a naturally occurring coenzyme chemically named 2,3-dimethoxy-5-methyl-6-decaprenyl-1,4-benzoquinone. Co-Q10 is also known by the names ubiquinone, ubidecarenone, and Vitamin Q and is classified as a fat soluble quinone.

U.S. Pat. No. 5,989,583 (Anselem) discloses that Co-Q10 is an antioxidant with potential use as a dietary supplement to protect against age-related degeneration and as an adjuvant vitamin to prevent or treat many diseases. The patent also discloses that supplementary Co-Q10 has also reportedly shown beneficial influences in periodontal disease, certain blood circulation diseases, impaired memory, fatigue, coronary disease, irregular heartbeat, high blood pressure, immune system impairment, and the aging process. Moreover, coenzyme Q10 has been reported to be capable of improving one's performance in sports by enhancing the uptake and processing of oxygen in cells.

As disclosed in WO 95/05164, Co-Q10 is crystalline at room temperature and has a melting point of 49° C. Due to its isoprenoid side chain, Co-Q10 is extremely lipophilic and practically insoluble in water. As such, the bioavailability of the compound, if administered orally, would be limited due to the hydrophilic nature of the gastrointestinal system.

Several patents and published PCT applications disclose methods and compositions for administration of Co-Q10 that are said to improve the bioavailability of the compound. For example, U.S. Pat. No. 6,056,971 (Goldman) discloses solubilizing water insoluble dietary supplements such as Co-Q10 in a solubilizing agent, generally a non-ionic surface active agent, and an edible polyhydric alcohol to provide a liquid composition that is administered in gelatin capsules. U.S. Pat. No. 4,483,873 (Ohashi et al.) discloses aqueous solutions of Co-Q10 containing hydrogenated lecithin. U.S. Pat. No. 4,572,915 (Crooks) provides non-aqueous compositions of fat solubilized nutrients that are formed by admixing the fat solubilized nutrient with polyethoxylated caster oil and a pharmaceutically acceptable water miscible polyol. U.S. Pat. No. 5,989,583 (Anselem) discloses a dry solid lipid composition comprising therapeutically active lipophilic compound, a lipid comprising at least one solid fat and at least one phospholipid. U.S. Pat. No. 6,045,826 (Borowy-Borowski et al.) discloses water-soluble compositions of lipophilic compounds such as Co-Q10 with a structurally defined solubilizing agent having both hydrophobic and hydrophilic moieties. Finally, published PCT application WO 95/05164 (Westesen et al.) discloses aqueous formulations of "sparingly soluble substances" such as Co-Q10 comprising colloidal particles of supercooled melts.

Methyl sulfonyl methane ("MSM"), also known as dimethyl sulfone or sulfonylbismethane, has been disclosed as having potential therapeutic effects. For example, Heshler has disclosed the oral administration of MSM to animals including humans for ameliorating symptoms of gastrointestinal upset (U.S. Pat. No. 4,514,421), for treating parasitic infections (U.S. Pat. No. 4,914,135), and for use as assimilable source of dietary sulfur for improving poor health and maintaining good health (U.S. Pat. No. 4,616,039). Further, U.S. Pat. No. 5,891,853 (Shealy et al.) discloses compositions comprising MSM, vitamin C and beta-1,3-glucan to enhance levels of dehydroepiandrosterone (DHEA) in humans.

Thus, a composition comprising Co-Q10 and MSM is desirable for nutritional and therapeutic benefits and for use in promoting general health maintenance. Further, a composition comprising Co-Q10 and MSM in an aqueous form is desirable for ease of administration and for the anticipated increase in bioavailability of the lipophilic nutrient component Co-Q10. Moreover, an aqueous composition comprising Co-Q10 and MSM in a formulation that remains in aqueous suspension without substantial separation for extended periods is desirable for incorporation into beverages and liquid forms that are intended to be stored for extended periods of time before consumption.

Therefore, it is an object of this invention to provide a composition comprising Co-Q10 and MSM. It is also an object of this invention to provide an aqueous dispersable formulation of Co-Q10 for oral administration. It is further an object of the invention to provide a stable aqueous formulation of lipophilic nutrients such as Co-Q10.

These and additional objects and advantages of the present invention are shown from the description below. The disclosures of the patents and publications cited throughout this specification are incorporated in their entirety to more fully describe the invention and to demonstrate the state of the art.

SUMMARY OF THE INVENTION

This invention provides compositions comprising coenzyme Q10, methyl sulfonyl methane, citric acid, and at least one polysorbate material.

The invention also provides stable aqueous compositions for oral administration to an animal comprising an admixture of coenzyme Q10, citric acid, methyl sulfonyl methane, and at least one polysorbate materials dispersed in an aqueous medium.

The invention further provides a method of administering a nutritionally significant amount of coenzyme Q10 to an animal which comprises administering to the animal a composition comprising coenzyme Q10, methyl sulfonyl methane, citric acid, and at least one polysorbate material.

The invention also provides a method of administering a therapeutically effective amount of coenzyme Q10 to an animal in need of such therapy which comprises administering to the animal a composition comprising coenzyme Q10, methyl sulfonyl methane, citric acid, and at least one polysorbate material.

DETAILED DESCRIPTION

This invention provides compositions comprising coenzyme Q10, methyl sulfonyl methane, citric acid, and at least one polysorbate material.

Those skilled in the art recognize that all the ingredients of the claimed composition are substances readily available through commercial sources. For example, Co-Q10 can be obtained from Seltzer Chemical Co. (Carlsbad, Calif.), methyl sulfonyl methane can be obtained from Carolwood Corp. (Greensville, Pa.), citric acid is available from Textile Chemical Co. (Reading, Pa.), polysorbate materials are available from Lipo Chemical (Paterson, N.J.). In a preferred embodiment, the compositions also comprise at least one water-soluble polysaccharide, which are available from Cerestar Co. (Hammond, Ind.). Maltodextrin is the preferred water-soluble polysaccharide for the claimed compositions and methods.

As used herein, the term polysorbate material encompasses the widely available Polysorbate or Tween products which comprise oleate esters of sorbitol and its anhydrides typically copolymerized with about 20 moles of ethylene oxide per mole of sorbitol and sorbitol anhydride. The polysorbate materials intended are those that are soluble or well dispersible in water. The oleate esters have the structure:

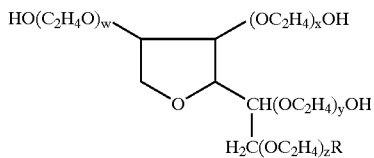

In a preferred embodiment, the polysorbate material is a sorbitan mono-9-octadecenoate poly(oxy-1,2-ethanediyl) derivative wherein the sum of w, x, y, and z is 80 (Tween 80 or Polysorbate 80).

In a preferred embodiment, the composition of the invention comprises about 0.1% to about 10% coenzyme Q10, about 0.1% to about 10% methyl sulfonyl methane, about 0.1% to about 15% polysorbate material, about 0.1% to about 10% citric acid, and about 45% to about 99.6% water-soluble polysaccharide. All percentages recited in this specification, unless otherwise indicated, are provided on a weight to weight basis based on the total weight of the composition.

In a particularly preferred embodiment, the composition comprises about 5% coenzyme Q10, about 5% methyl sulfonyl methane, about 10% polysorbate material, about 0.5% citric acid, and about 79.5% water-soluble polysaccharide.

The composition of the invention is prepared by first heating the polysorbate material to between 35° C. to 60° C. in a steam jacketed planetary mixer or equivalent heating device. Coenzyme Q10 is then added and mixed until dissolved. The citric acid is then mixed in until a uniform mixture is formed. Methyl sulfonyl methane is added next and mixed to form a uniform mixture. Lastly, the optional water-soluble polysaccharide, such as maltodextrin, is added and mixed for between 5 and 20 minutes. It is not critical that the components be added in the exact order recited. However adding the coenzyme Q10 to preheated polysorbate material is preferred.

The mixture is formed as a paste and can be used as such in the methods or products described herein. If desired, the mixture can also be formed into a powder, for example by spray drying, granulated, and included in a product or used in any of the methods described herein.

The composition of the invention is characterized by its ability to form stable dispersions of the highly lipophilic nutrient coenzyme Q10 in aqueous medium. As used herein the term stable aqueous composition refers to dispersions of the coenzyme Q10 composition of the invention in water or other aqueous solvent that remain in suspension, whereby any portion of the composition that percipitates can be resuspended readily by agitating the solution. As demonstrated below, the composition of the invention was readily suspended in water at varying concentrations and remained as stable aqueous compositions for at least three weeks.

Thus, the invention also provides a stable aqueous composition for oral administration to an animal comprising an admixture of coenzyme Q10, citric acid, methyl sulfonyl methane, and at least one polysorbate material dispersed in an aqueous medium. In a preferred embodiment, the admixture also comprises at least one water-soluble polysaccharide. As used herein, the term animals includes humans and, in a preferred embodiment, the compositions and methods of the invention are administered to humans. According to this aspect of the invention, the admixture of coenzyme Q10, citric acid, methyl sulfonyl methane, at least one polysorbate material and the optional at least one water-soluble polysaccharide is formed prior to contacting with the aqueous medium.

In a preferred embodiment of the stable aqueous composition, the admixture comprises about 0.1% to about 10% coenzyme Q10, about 0.1% to about 10% methyl sulfonyl methane, about 0.1% to about 15% polysorbate material, about 0.1% to about 10% citric acid, and about 45% to about 99.6% water-soluble polysaccharide.

In a particularly preferred embodiment of the stable aqueous composition, the admixture comprises about 5% coenzyme Q10, about 5% methyl sulfonyl methane, about 10% polysorbate material, about 0.5% citric acid, and about 79.5% water-soluble polysaccharide.

As used herein the aqueous medium can comprise water or other aqueous solvents suitable for consumption. In a preferred embodiment treated water is contemplated as the aqueous medium for this invention. Treated water has substantially all mineral content of the water removed prior to supplementation with the Co-Q10 composition disclosed herein. Methods of producing treated water are known to those of ordinary skill in the art and include deionization, distillation, filtration and reverse osmosis ("R-O"), among others. The terms "treated water", "purified water", "demineralized water", "distilled water" and "R-O water" are understood to be synonymous herein.

By its ability to readily form dispersions in aqueous medium, the invention therefore provides the highly lipophilic Co-Q10 in a bioavialable form for absorption in the hydrophilic gastrointestinal system. The composition of the invention therefore provides a means for oral administration of Co-Q10 to an animal in a form that delivers a nutritionally significant amount of Co-Q10. As used herein, a nutritionally significant amount of Co-Q10 is understood to be an amount at least about 1%, and preferably at least 10%, of the U.S. Recommended Daily Allowance ("RDA") of Co-Q10 per serving of a beverage or food product containing the Co-Q10 composition of the invention. At present, the RDA for humans is between 60 mg and 120 mg Co-Q10 per day.

Thus, the invention also provides a method of administering a nutritionally significant amount of coenzyme Q10 to an animal which comprises administering to the animal a composition comprising coenzyme Q10, methyl sulfonyl methane, citric acid, and at least one polysorbate material. In a preferred embodiment the composition also comprises at least one water-soluble polysaccharide.

In a preferred embodiment of this method, the composition administered comprises about 0.1% to about 10% coenzyme Q10, about 0.1% to about 10% methyl sulfonyl methane, about 0.1% about 15% polysorbate material, about 0.1% to about 10% citric acid, and about 45% to about 99.6% water-soluble polysaccharide.

In a particularly preferred embodiment of this method, the composition comprises about 5% coenzyme Q10, about 5% methyl sulfonyl methane, about 10% polysorbate material, about 0.5% citric acid, and about 79.5% water-soluble polysaccharide.

Although characterized by its ability to form stable aqueous dispersions, the compositions of the invention, including the composition administered in the method of the invention, are not limited to aqueous forms. As described above, the Co-Q10 composition is produced as a paste that can be used as is or dried to form a powder. The composition can then be incorporated into medicaments, dietary supplements, food products or beverages by methods known to those of ordinary skill in the art. Examples of suitable food products include baked goods and non-baked goods such as nutritional bars, muffins, breads, cakes, energy gels, drink mixes and the like. Examples of beverages include flavored and unflavored waters, energy drinks, sports drinks, carbonated and non-carbonated soft drinks, teas and the like. The composition can also be used as an additional ingredient in dietary formulations of processed and non-processed foods.

Those skilled in the art recognize that a dietary supplement containing the composition of the invention and foods, beverages, or medicaments containing the Co-Q10 composition of the invention can be the same form, differing only by the amount of coenzyme Q10 included in each. When the amount of coenzyme Q10 incorporated in a food, beverage, or medicament rises to a level of providing recommended daily values they are referred to as dietary supplements. Thus, for example, dietary supplements can also be pills, tablets, capsules, powders, baked and non-baked goods, or carbonated and non-carbonated beverages, and the like depending on the amount of coenzyme Q10 incorporated.

The Co-Q10 composition may also be administered orally in unit dosage form as an aqueous composition administered by oral drops or in any of the usual solid forms such as pills, tablets, capsules or powders, including sustained release preparations. Capsules made from gelatin are preferred. Such pills, tablets, capsules and powders incorporating the Co-Q10 composition of the invention can be prepared by standard methods known to those of ordinary skill in the art.

The term unit dosage form as used in this specification and the claims refer to physically discrete units to be administered in single or multiple dosage to animals including humans, each unit containing a predetermined quantity of active material, i.e., coenzyme Q10 and/or MSM, optionally in association with one or more carriers. The quantity of active material is that amount calculated to produce the desired nutritional or therapeutic effect upon administration of one or more of such units. Of course, it is understood that the exact treatment level will depend upon the case history of the subject to be treated. The precise treatment level can be determined by one of ordinary skill in the art without undue experimentation, taking into consideration such factors as age, size, severity of condition, and anticipated duration of administration of compounds, among other factors known to those of ordinary skill.

Unit dosages can range from about 1.0 mg/kg to about 100 mg/kg (the unit designated "mg/kg" as used herein refers to mg of coenzyme Q10 and/or MSM per kilogram of body weight), preferably from about 10 mg/kg to about 30 mg/kg, most preferably about 20 mg/kg. The doses can be administered in any convenient dosing schedule to achieve the stated beneficial effects. For example, the doses can be taken 1, 2, 3, 4, 5 or more times daily. Preferably 3 doses are taken daily. Most preferably, the doses are taken at meal times.

Finally, the invention also provides a method of administering a therapeutically effective amount of coenzyme Q10 to an animal in need of such therapy which comprises administering to the animal a composition comprising coenzyme Q10, methyl sulfonyl methane, citric acid, and at least one polysorbate material. In a preferred embodiment the compositions also comprises at least one water-soluble polysaccharide.

As used herein, the term therapeutically effective amount refers to an amount of coenzyme Q10, typically as part of the composition of the invention in unit dosage form, that is effective to treat, prevent, or alleviate the symptoms of a disease. Examples of diseases that are susceptible to treatment and prophylaxis by administration of coenzyme Q10 include periodontal disease, certain blood circulation diseases, impaired memory, fatigue, coronary disease, irregular heartbeat, high blood pressure, immune system impairment, and diseases associated with the aging process.

In a preferred embodiment of this method, the composition administered comprises about 0.1% to about 10% coenzyme Q10, about 0.1% to about 10% methyl sulfonyl methane, about 0.1% to about 15% polysorbate material, about 0.1% to about 10% citric acid, and about 45% to about 99.6% water-soluble polysaccharide.

In a particularly preferred embodiment of this method, the composition comprises about 5% coenzyme Q10, about 5% methyl sulfonyl methane, about 10% polysorbate material, about 0.5% citric acid, and about 79.5% water-soluble polysaccharide.

The following examples are provided for illustrative purposes only. They are not intended, and should not be interpreted, to limit the scope of the invention which is more fully set forth in the claims which follow thereafter.

EXAMPLE 1

An aqueous dispersable coenzyme Q10 composition according to the invention was prepared as follows (all percentages are by weight of the total composition):

| | |
|---|---|
| Tween 80 | 10% |
| Citric Acid | 0.5% |
| MSM | 5% |
| Co-Q10 | 5% |
| Maltodextrin | 79.5% |
| Total | 100% |

The polysorbate 80 (Lipo Chemical., Paterson, N.J.) was heated to between 35° C. to 60° C. in a steam jacketed planetary mixer and then coenzyme Q10 (Seltzer Chemical Co., Carlsbad, Calif.) was added and mixed until dissolved. The citric acid (Textile Chemical Co., Reading, Pa.) was then mixed in until a uniform mixture is formed and then the methyl sulfonyl methane (Carolwood Corp., Greensville, Pa.) was added and mixed to form a uniform mixture. Finally, the maltodextrin (Cerestar Co., Hammond, Ind.) was added and mixed for between 5 and 20 minutes. The combined ingredients formed a paste.

EXAMPLE 2

Dissolution of the Coenzyme Q10 Formulation

As a highly lipophilic compound, coenzyme Q10 alone is not water soluble at any level. As demonstrated in this example, the aqueous dispersable Co-Q10 composition of the invention is demonstrated to maintain coenzyme Q10 as a stable aqueous composition for at least 3 weeks at various concentrations. Any coenzyme Q10 that appeared to precipitate out was easily resuspended by simple inversion.

Four 100 mL volumetric flasks were filled to approximately one half volume with deionized water at room temperature.

Aliquots of 0.1 gram, 0.25 gram, 0.5 gram, and 1.0 gram of the Co-Q10 composition prepared in accordance with Example 1 were weighed. Each of the individual composition aliquots were added to the individual volumetric flasks. The flasks were shaken by hand until most of the Co-Q10 composition had become dispersed. Each flask was then brought to 100 ml volume with deionized water and any remaining Co-Q10 composition dispersed.

The final concentration of coenzyme Q10 in each of the individual flasks were 0.05mg/mL, 0.125 mg/mL, 0.25 mg/mL and 0.5 mg/mL (based on coenzyme Q10 representing 5% (w/w) of the Co-Q10 composition prepared in Example 1). The aqueous compositions appeared to be saturated at the highest concentration.

The flasks were allowed to remain at room temperature for three weeks and were visually inspected daily to determine the stability of the Co-Q10 composition of the invention.

After four days, the Co-Q10 composition remained as a stable suspension in all of the flasks. By the fifth day some of the Co-Q10 composition from 0.25 mg/ml and 0.5 mg/mL concentrations began to settle to the bottom of the flasks. This sediment was resuspended by simple inversion of the flasks.

At the end of three weeks, approximately one half of the Co-Q10 composition from each of the flasks had precipitated out and settled to the bottom of the flasks. Again, the sediment was resuspended by simple inversion.

EXAMPLE 3

The lowest concentration from Example 2 (0.05 mg/mL) was not expected to stay in suspension as long as it did because of the large dilution factor. A 0.1 g aliquot of the Co-Q10 composition of the invention added to 100 mL of water represents a 1000×dilution. At this dilution the hydrogen bonding properties of the water would be expected to overcome any surfactant properties of the composition and cause the coenzyme Q10 itself to precipitate immediately. Since it stayed in solution, it was postulated, without being bound by theory, that there is some interaction between the coenzyme Q10 and the remaining components of the composition of the invention which is necessary to keep the coenzyme Q10 in suspension.

To test this theory a 1%, 2.5% and 5% aqueous solutions of the all the composition ingredients except coenzyme Q10 were made in 100 mL volumetric flasks. A 5 mg aliquot of coenzyme Q10 was then separately added to each of the flasks and shaken. It was noticed that the separately-added coenzyme Q10 did not go into solution or form a dispersion in any of the flasks. Even when placed in an ultra sound bath, the separately-added coenzyme Q10 dispersed then settled to the bottom of the flask.

What is claimed is:

1. A composition comprising coenzyme Q10, methyl sulfonyl methane, citric acid, and at least one polysorbate material.

2. The composition of claim 1 further comprising at least one water-soluble polysaccharide.

3. The composition of claim 2 comprising about 0.1% to about 10% coenzyme Q10, about 0.1% to about 10% methyl sulfonyl methane, to about 0.1% and about 15% polysorbate material, about 0.1% to about 10% citric acid, and about 45% to about 99.6% water-soluble polysaccharide.

4. The composition of claim 3, wherein the water-soluble polysaccharide is maltodextrin.

5. A food product comprising the composition of claim 1.

6. A beverage comprising the composition of claim 1.

7. The composition of claim 1 in unit dosage form.

8. A stable aqueous composition for oral administration to an animal comprising an admixture of coenzyme Q10, citric acid, methyl sulfonyl methane, at least one polysorbate material dispersed in an aqueous medium.

9. The stable aqueous composition of claim 8 further comprising at least one water-soluble polysaccharide.

10. The stable aqueous composition of claim 9, wherein the admixture comprises about 0.1% to about 10% coenzyme Q10, about 0.1% to about 10% methyl sulfonyl methane, about 0.1% to about 15% polysorbate material, about 0.1% to about 10% citric acid, and about 45% to about 99.6% water-soluble polysaccharide.

11. The stable aqueous composition of claim 10, wherein the water-soluble polysaccharide is maltodextrin.

12. The stable aqueous composition of claim 8, wherein the aqueous medium is water.

13. A beverage comprising the stable aqueous composition of claim 8.

14. A method of administering a nutritionally significant amount of coenzyme Q10 to an animal which comprises administering to the animal a composition comprising coenzyme Q10, methyl sulfonyl methane, citric acid, and at least one polysorbate material.

15. The method of claim 14 wherein the composition further comprises at least one water-soluble polysaccharide.

16. The method of claim 15, wherein the composition comprises about 0.1% to about 10% coenzyme Q10, about 0.1% to about 10% methyl sulfonyl methane, about 0.1% to about 15% polysorbate material, about 0.1% to about 10% citric acid, and about 45% to about 99.6% water-soluble polysaccharide.

17. The method of claim 16, wherein the water-soluble polysaccharide is maltodextrin.

18. The method of claim 14, wherein a food product comprising the composition is administered to the animal.

19. The method of claim 14, wherein a beverage comprising the composition is administered to the animal.

20. The method of claim 14, wherein the composition is administered in unit dosage form.

21. A method of administering a therapeutically effective amount of coenzyme Q10 to an animal in need of such therapy which comprises administering to the animal a composition comprising coenzyme Q10, methyl sulfonyl methane, citric acid, and at least one polysorbate material.

22. The method of claim 21, wherein the composition further comprises at least one water-soluble polysaccharide.

23. The method of claim 22, wherein the composition comprises about 5% coenzyme Q10, about 5% methyl sulfonyl methane, about 10% polysorbate material, about 0.5% citric acid, and about 79.5% water-soluble polysaccharide.

24. The method of claim 23, wherein the water-soluble polysaccharide is maltodextrin.

* * * * *